(12) United States Patent
Ohlhausen et al.

(10) Patent No.: US 8,257,780 B2
(45) Date of Patent: *Sep. 4, 2012

(54) THERAPEUTIC COMPOSITION CONTAINING AN ORGANOSILANE QUATERNARY COMPOUND AND HYDROGEN PEROXIDE FOR TREATING SKIN DISORDERS AND METHODS OF USING

(75) Inventors: Howard G. Ohlhausen, Paradise Valley, AZ (US); Jerome H. Ludwig, Sun City West, AZ (US)

(73) Assignee: Resource Development L.L.C., Scottsdale, AZ (US)

( * ) Notice: Subject to any disclaimer, the term of this patent is extended or adjusted under 35 U.S.C. 154(b) by 495 days.

This patent is subject to a terminal disclaimer.

(21) Appl. No.: 11/284,374

(22) Filed: Nov. 21, 2005

(65) Prior Publication Data

US 2006/0110348 A1 May 25, 2006

Related U.S. Application Data

(63) Continuation-in-part of application No. 10/698,313, filed on Oct. 31, 2003, now Pat. No. 6,994,890.

(51) Int. Cl.
*A61K 31/70* (2006.01)
*A61K 33/40* (2006.01)
(52) U.S. Cl. .......................... 427/62; 424/70.1; 424/616
(58) Field of Classification Search .................. None
See application file for complete search history.

(56) References Cited

U.S. PATENT DOCUMENTS

| | | | |
|---|---|---|---|
| 2,612,458 A | 9/1952 | Stedman | 117/92 |
| 2,923,653 A | 2/1960 | Matlin et al. | 154/101 |
| 2,962,390 A | 11/1960 | Fain et al. | 117/64 |
| 3,130,164 A | 4/1964 | Best | 252/99 |
| 3,244,541 A | 4/1966 | Fain et al. | 106/13 |
| 3,560,385 A | 2/1971 | Roth | 252/49.6 |
| 3,579,540 A | 5/1971 | Ohlhausen | 260/33.4 |
| 3,730,701 A | 5/1973 | Isquith et al. | 71/67 |
| 3,794,736 A | 2/1974 | Abbott et al. | 424/78 |
| 3,817,739 A | 6/1974 | Abbott et al. | 71/67 |
| 3,860,709 A | 1/1975 | Abbott et al. | 424/184 |
| 3,865,728 A | 2/1975 | Abbott et al. | 210/169 |
| 3,954,974 A | 5/1976 | Herzog et al. | |
| 4,005,025 A | 1/1977 | Kinstedt | 252/89 R |
| 4,005,028 A | 1/1977 | Heckert et al. | 252/99 |
| 4,005,030 A | 1/1977 | Heckert et al. | 252/140 |
| 4,161,273 A | 7/1979 | Wen et al. | 424/52 |
| 4,259,103 A | 3/1981 | Malek et al. | 71/67 |
| 4,282,366 A | 8/1981 | Eudy | 556/413 |
| 4,311,598 A | 1/1982 | Verachtert | 210/757 |
| 4,361,273 A | 11/1982 | Levine et al. | 236/11 |
| 4,390,712 A | 6/1983 | Karl et al. | 556/413 |
| 4,394,378 A | 7/1983 | Klein | 424/184 |
| 4,397,757 A | 8/1983 | Bright et al. | 252/186.41 |
| 4,406,892 A | 9/1983 | Eudy | 424/184 |
| 4,421,796 A | 12/1983 | Burril et al. | 427/387 |
| 4,430,236 A | 2/1984 | Franks | 252/95 |
| 4,467,013 A | 8/1984 | Baldwin | 428/289 |
| 4,567,039 A | 1/1986 | Stadnick et al. | 132/70 |
| 4,576,728 A | 3/1986 | Stoddart | 252/102 |
| 4,615,882 A | 10/1986 | Stockel | 424/80 |
| 4,631,273 A | 12/1986 | Blehm et al. | 514/29 |
| 4,682,992 A | 7/1987 | Fuchs | 55/279 |
| 4,781,974 A | 11/1988 | Bouchette et al. | 428/288 |
| 4,797,420 A | 1/1989 | Bryant | 514/643 |
| 4,826,681 A * | 5/1989 | Jacquet et al. | 424/613 |
| 4,835,019 A | 5/1989 | White et al. | 427/387 |
| 4,842,766 A | 6/1989 | Blehm et al. | 252/309 |
| 4,847,088 A | 7/1989 | Blank | 424/404 |
| 4,866,192 A | 9/1989 | Plueddemann et al. | 556/410 |
| 4,908,355 A | 3/1990 | Gettings et al. | |
| 4,941,989 A | 7/1990 | Kramer et al. | 252/102 |
| 4,990,377 A | 2/1991 | Wilson | 427/387 |
| 4,999,249 A | 3/1991 | Deschler et al. | 428/447 |
| 5,013,459 A | 5/1991 | Gettings et al. | 210/764 |
| 5,209,775 A | 5/1993 | Bank et al. | 106/2 |
| 5,320,805 A | 6/1994 | Kramer et al. | 422/28 |
| 5,348,556 A | 9/1994 | Minns et al. | 8/137 |
| 5,360,568 A | 11/1994 | Madison et al. | 252/102 |
| 5,360,569 A | 11/1994 | Madison et al. | 252/102 |
| 5,411,585 A | 5/1995 | Avery et al. | 106/287.1 |
| 5,478,357 A | 12/1995 | Madison et al. | 8/111 |
| 5,552,476 A | 9/1996 | Halling | 524/837 |
| 5,620,527 A | 4/1997 | Kramer et al. | 134/2 |
| 5,736,582 A | 4/1998 | Devillez et al. | |

(Continued)

FOREIGN PATENT DOCUMENTS

CA 1010782 5/1977

(Continued)

OTHER PUBLICATIONS

Material Safety Data Sheet, "Hydrogen Peroxide (20 to 40%)," FMC Incorporation, Jun. 2008, pp. 1-11.* PCT/US2006/043351 International Search Report and Written Opinion of the International Search Authority, mailed Jul. 27, 2007.
Reregistration Eligibility Decision for Trimethoxysilyl Quaternary Ammonium Chloride Compounds; including letter from Frank T. Sanders and Table of Contents, p. 3 of Reregistration Eligibility Decision; EPA 739-R-07-007, Case No. 3148, Sep. 25, 2007.
Witucki, Gerald L.; A Silane Primer: Chemistry and Applications of Alkoxy Silanes; Dow Corning Corporation, Journal of Coatings Technology Reprint, presented on Oct. 21, 1992.
Inorganic Chemistry: An Advanced Textbook, Chapter 14, "The Oxygen Family", Hydrogen Peroxide, pp. 504-506 (1954).
Material Safety Data Sheet for ZTREX 72 Antimicrobial Agent MUP, Piedmont Chemical Industries I, LLC, Apr. 28, 2006. (3 pages.).
Material Safety Data Sheet for Q9-6346 Silane, Dow Corning Corporation, Jan. 1, 2002. (9 pages).
PAN Pesticides Database—Pesticide Products, Ztrex 72 antimicrobial mup; http://www.pesticideinfo.org; Jul. 3, 2007. (4 pages).

*Primary Examiner* — Daniel Sullivan
*Assistant Examiner* — Rachael E Bredefeld
(74) *Attorney, Agent, or Firm* — Wood, Herron & Evans, LLP

(57) ABSTRACT

Therapeutic skin cleansing and multifunctional coating compositions containing hydrogen peroxide and an organosilane quaternary compound in aqueous formulations are used to treat skin disorders including wounds, abrasions, ulcers, burns, infections, irritations, microbes, soil, water, psoriasis, acne vulgaris, blemishes, age spots, sclerosis, other physical or chemical injuries, and other skin deficiencies.

22 Claims, No Drawings

U.S. PATENT DOCUMENTS

| | | | |
|---|---|---|---|
| 5,798,144 A | 8/1998 | Varanasi et al. | 427/384 |
| 5,954,869 A | 9/1999 | Elfersy et al. | 106/287.16 |
| 5,959,014 A | 9/1999 | Liebeskind et al. | 524/389 |
| 6,087,319 A | 7/2000 | Norman | 510/466 |
| 6,113,815 A | 9/2000 | Elfersy et al. | 252/588 |
| 6,120,587 A | 9/2000 | Elfersy et al. | 106/18.35 |
| 6,218,351 B1 | 4/2001 | Busch et al. | 510/311 |
| 6,221,944 B1 | 4/2001 | Liebeskind et al. | 524/386 |
| 6,240,929 B1 | 6/2001 | Richard et al. | 132/202 |
| 6,309,425 B1 | 10/2001 | Murphy | 81/42 |
| 6,316,399 B1 | 11/2001 | Melikyan et al. | 510/372 |
| 6,346,279 B1 | 2/2002 | Rochon | 424/616 |
| 6,361,787 B1 | 3/2002 | Shaheen et al. | 424/406 |
| 6,372,702 B1 | 4/2002 | Chiou et al. | 510/222 |
| 6,376,448 B1 | 4/2002 | Colurciello, Jr. et al. | |
| 6,391,840 B1 | 5/2002 | Thompson et al. | 510/376 |
| 6,403,547 B1 | 6/2002 | Grippaudo et al. | 510/280 |
| 6,417,151 B1 | 7/2002 | Grothus et al. | 510/312 |
| 6,432,181 B1 | 8/2002 | Ludwig | 106/2 |
| 6,436,445 B1 | 8/2002 | Hei et al. | 424/667 |
| 6,461,537 B1 | 10/2002 | Turcotte et al. | 252/194 |
| 6,488,965 B1 * | 12/2002 | Karageozian | 424/665 |
| 6,530,384 B1 | 3/2003 | Meyers et al. | 134/25.2 |
| 6,534,075 B1 | 3/2003 | Hei et al. | 424/405 |
| 6,548,467 B2 | 4/2003 | Baker et al. | 510/312 |
| 6,610,777 B1 | 8/2003 | Anderson et al. | 524/588 |
| 6,613,755 B2 | 9/2003 | Peterson et al. | 514/63 |
| 6,994,890 B2 * | 2/2006 | Ohlhausen et al. | 427/393.4 |
| 2002/0111282 A1 | 8/2002 | Charaf et al. | |
| 2004/0096260 A1 * | 5/2004 | Rhoades | 401/8 |
| 2005/0096250 A1 | 5/2005 | Ohlhausen et al. | |
| 2007/0010419 A1 * | 1/2007 | Ohlhausen et al. | 510/368 |
| 2007/0227557 A1 * | 10/2007 | Ohlhausen et al. | 134/4 |

FOREIGN PATENT DOCUMENTS

| | | |
|---|---|---|
| CA | 1217004 | 1/1987 |
| DE | 19538629 A | 4/1997 |
| WO | WO 00/54587 | 9/2000 |
| WO | WO 00/72850 | 12/2000 |
| WO | 2005/042657 | 5/2005 |
| WO | 2006/086271 | 2/2006 |
| WO | 2007/008239 | 1/2007 |

OTHER PUBLICATIONS

* cited by examiner

THERAPEUTIC COMPOSITION CONTAINING AN ORGANOSILANE QUATERNARY COMPOUND AND HYDROGEN PEROXIDE FOR TREATING SKIN DISORDERS AND METHODS OF USING

RELATED APPLICATION

This application is a continuation-in-part application of U.S. patent application Ser. No. 10/698,313, filed Oct. 31, 2003, U.S. Publication No. 2005/0096250, published May 5, 2005 (Ohlhausen and Ludwig), now U.S. Pat. No. 6,994,890 entitled "Cleaning and Multifunctional Coating Composition Containing Organosilane QuaternaryCompound and Methods of Using." That application is incorporated herein by reference in its entirety for all benefits and purposes in understanding the inventions described and claimed hereinafter.

FIELD OF THE INVENTION

This invention relates to therapeutic compositions for treating skin disorders. Organosilane quaternary nitrogen compounds are formulated with the hydrogen peroxide in aqueous media to provide compositions that can be applied to skin for treatment or prevention of disorders or conditions related to skin surface properties.

BACKGROUND OF THE INVENTION

Skin is one of the largest organs in the body and covers substantially the entire body surface. Skin is composed of two main layers: the surface epithelium or epidermis which includes the uppermost stratum corneum, and the subjacent connective tissue layer or dermis. The skin has a number of functions such as protecting an organism from injury and dessication, receiving environmental stimuli, excreting various substances, regulating body temperature and helping to maintain water balance. Because of its quantitative and qualitative importance, substantially intact and healthy skin is crucial not only for the well being of an organism but for its very survival.

The health and integrity of skin may be compromised by wounds, abrasions, ulcers, burns, infections, irritations, microbes, soil, water, other physical or chemical injuries, and other conditions for which normal skin production and repair processes may be inadequate. For example, acute conditions such as patients who are burned over a large surface area often require immediate skin replacement. Less life-threatening but chronic skin problems such as decubitus ulcers, psoriasis, acne vulgaris, blemishes, age spots, sclerosis, or irritations from diaper rash may progress to more severe conditions if left untreated. Skin treatments encompass a variety of methods and products. These may range from symptomatic treatments such as the use of topical anti-inflammatory compounds to the use of replacement skin.

Exposure of the skin to water over a prolonged time period produces deleterious effects on the integrity and condition of the skin, such as maceration and damage to the barrier function of skin. For example, long term water exposure is a known cause of dermatitis. Dermatitis, defined as an inflammation of the skin, is a major problem in professions in which a portion of the skin is subject to prolonged water exposure (the so-called "wet professions"). Soldiers serving in tropical climates are also known to suffer from painful swollen feet ("tropical immersion foot") due to long term water exposure. Such situations comprise a large part of occupational medicine and have a significant economic impact. Thus, there is a need for treatment and prevention of these deleterious effects on the skin.

It has been established that the water and soil repellency of surfaces can be improved by the use of silicone compositions. There has been extensive research and development involving silicone compositions for rendering surfaces water repellent. U.S. Pat. No. 3,579,540 (Ohlhausen) discloses water repellent film-forming compositions of alkylpolysiloxanes, acid and solvent which result in durable and effective water repellent films on various surfaces. Further improvements in solventless compositions for treating porous and nonporous surfaces have been made as disclosed in U.S. Pat. No. 6,432,181 (Ludwig and Ohlhausen). The '181 patent satisfied a need which existed for soil and water repellent compositions that eliminate solvents and utilize the silicone more effectively and economically. Additional improvements in soil and water repellent compositions were made by providing physiologically acceptable compositions that were non-corrosive and non-irritating to the eyes and skin of the user in accordance with Federal Hazard Substances Act and Consumer Product Safety Commission 16 CFR 1500 Guidelines as disclosed in U.S. Pat. No. 6,676,733 (Ludwig and Ohlhausen).

Many different types of hard and soft surfaces have also been rendered antimicrobial by coating with different agents. Organosilane quaternary nitrogen compounds have also been employed effectively in eliminating and/or reducing microbial contamination when applied to a variety of surfaces. For instance, bacterial, viral and fungal contamination may be eliminated or reduced when such organosilane quaternary compounds are applied to surfaces. Commercially available quaternary ammonium organosilanes which have been used for this purpose include 3-(trimethoxysilyl)propyldimethyloctadecyl ammonium chloride, 3-(trimethoxysilyl)propyldidecylmethyl ammonium chloride, and 3-(trimethoxysilyl)propyltetradecyldimethyl ammonium chloride. The following patents and patent applications disclose the use of siliconized and/or non-siliconized quaternaries, solvents and sufactants/detergents for the cleaning and/or water repellent treatment of substrates: U.S. Pat. No. 4,005,028; U.S. Pat. No. 4,005,030; U.S. Pat. No. 6,559,111; U.S. Pat. No. 6,897,191; U.S. Pat. No. 6,809,072; U.S. Publ. No. 2005/0089695; U.S. Publ. No. 2005/0020474; U.S. Publ. No. 2003/0109395; U.S. Pat. No. 6,881,247; U.S. Pat. No. 5,426,204; U.S. Pat. No. 4,908,355; and U.S. Pat. No. 6,613,755.

Compositions and processes for medicating human skin disorders using hydrogen peroxide as an active antimicrobial agent are very well known. Compositions which include essentially hydrogen peroxide in aqueous media or with volatile and non-volatile carrier-solvents have been routinely used. Other therapeutic agents have been added to the hydrogen peroxide compositions for treating various skin ailments. Accordingly, pharmaceutical and cosmetic compositions have been disclosed in the patent art, and the following patents are representative of such disclosures, including: U.S. Pat. Nos. 5,906,810; 5,958,984; 5,380,764; 4,826,681; and 3,954,974; and U.S. Publ. No. 2003/0008018.

It had previously been established with reference to our earlier application U.S. Ser. No. 10/698,313, filed Oct. 31, 2003, now U.S. Pat. No. 6,994,890, that the organosilane quat in combination with the hydrogen peroxide had surfactant properties which enable a soiled surface to be cleaned and simultaneously rendered water and soil repellent, as well as antimicrobial. Accordingly, everyday surfaces that are soiled with everyday household soil that results from cooking, eating, washing, etc., may be simultaneously cleaned and provided with a bonded organosilane quaternary coating that rather durably repels water and soil while having antimicrobial properties.

As also reported in our earlier '313 application, the organosilane quat in combination with the hydrogen peroxide provides synergistic results upon bonding onto surfaces. The inventive composition containing the combination of the organosilane quat and hydrogen peroxide components provides unexpectedly improved bonding and durability of the composition on various surfaces. In other words, the results achieved with the combined components in the composition exceeds the expected algebraic sum of the activity of each component when separately used on the surface. These synergistic activities contribute to unique compositions and methods.

SUMMARY OF THE INVENTION

It has now been found that compositions reported in our earlier '313 application have therapeutic properties when applied to skin. In particular, skin which has been compromised by any of a number of disorders has been repaired by using the inventive composition. In other aspects, the compositions have been found to remedy, cure and/or prevent skin deficiencies caused by water, soil, and/or microbes. The composition comprises a cationic organosilane quaternary ammonium compound ("organosilane quat") and hydrogen peroxide in aqueous media. These components are contained in effective amounts for treating skin whose integrity and health have been compromised by wounds, abrasions, infections, germs, irritations, soil, water, and other physical or chemical injuries.

Generally, the composition contains the organosilane quat in an amount up to about 5% by weight, normally about 1 to 5% by weight. Hydrogen peroxide or a complex thereof is in an amount up to 20% by weight, preferably about 3 to about 10% by weight. A liquid diluent is preferably employed and usually consists of deionized water and/or a solvent such as an alcohol, polyol, glycolether and mixtures thereof, for example, glycol, ethylene glycol monobutyl ether, methanol, ethanol, isopropanol, propanol, butanol, or the like. Compositions have pHs on the order of about 2 to about 9, preferably 3 to about 5. Above and below these pHs, nonreactivity of the components may be reduced, thereby diminishing the storage stability of the composition. The compositions may also contain an additive such as a thickener, gelling agent, lubricant, and solvent, and effective mixtures thereof.

As provided in more detail hereinafter, a number of therapeutic effects on the skin are achieved by compositions of this invention. In addition to its remedial or curative effects on skin which has been compromised by wounding, abrasion, microbial contamination, etc., the composition of this invention can be applied to the skin in an amount that is effective to cleanse the skin and improve its water repellency, i.e., its "hydrophobicity". Thus, the deleterious effects produced on the integrity and condition of the skin by exposure to water, such as maceration and damage to the barrier function of the skin, are alleviated or prevented by application of the inventive compositions. Importantly, the compositions may be formulated as a cream, a lotion, a gel, an ointment or a spray, etc., in order to take advantage of their effectiveness.

When employed to promote skin cleansing, the inventive compositions include, optionally, abrasive particles in an amount up to about 35% by weight, preferably about 5% to about 25% by weight. The abrasive particles facilitate the removal of dirt, grime and stains from skin that may be soiled as the result of working, environmental conditions, etc. The optional nonreactive abrasive particles may be coated or uncoated and typically consist of silicas ($SiO_2$), silicates, metal oxides, metal carbonates (calcium carbonate or coated calcium carbonate), clays, carbides and plastics, having an average size on the order of about 5 to about 300 microns.

This invention is also directed to a method of regulating the skin hydration by applying the composition of the organosilane quat and hydrogen peroxide to the skin in an effective amount to regulate hydration by providing a moisture transmissive coating.

The invention also involves a method for treating skin with a composition that provides a therapeutic multifunctional coating. For example, skin soiled with dirt, grime and stains that result from working, etc., may be cleaned and provided with the multifunctional coating upon application of the inventive composition. For example, a liquid inventive composition can be applied by wiping or spraying onto a soiled skin surface in an effective amount and the soil is removed by wiping. Upon such application, the surface becomes clean and an invisable, durable prophylactic coating is bonded onto the surface thereby forming a clean, water and soil repellent and antimicrobial surface that is not readily rinsed off. The coating is also moisture transmissive to allow for skin hydration and the regulation of hydration.

A further understanding of the invention, its various embodiments and operating parameters will be apparent with reference to the following detailed description.

DETAILED DESCRIPTION OF THE INVENTION

In accordance with the above summary, the objectives of this invention are to provide therapeutic compositions and methods for treating skin disorders. Among those skin disorders which have been remedied, healed and/or prevented successfully by the compositions of this invention are skin fungus (toe nail fungus); foot odor; hand and/or foot calluses; elbow and cradle cap psoriasis; skin tags (eye lid and/or nose); "age spots" (hands and/or face); pimples, zits and blackheads (acne); suspected basil cell carcinoma; paper cuts on hands; knee abrasion; "jock itch"; and puncture wounds, bacterial infections and other skin eruptions. The composition also provides for simultaneous cleaning, disinfecting and rendering the skin water and soil repellent. The therapeutic compositions are also (1) biodegradable, (2) skin penetrating and moisture transmissive, (3) broadband antimicrobial, (4) skin bondable and durably water and soil repellent, (5) storage stable and economical in terms of performance and coverage, and (6) can be used or applied as a cream, lotion, gel or ointment with ordinary techniques.

Organosilane Quaternary Ammonium Compounds

The organosilane quats are defined by the formula:

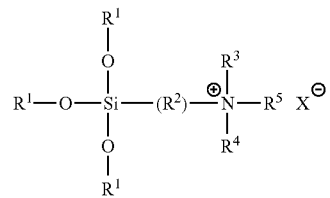

wherein $R^1$=hydrogen and/or $C_1$ to $C_4$ alkyl; $R^2$=divalent hydrocarbon radical with $C_1$ to $C_8$ carbon atoms, $R^3$=hydrogen or $C_1$ to $C_4$ alkyl, $R^4$=hydrogen or $C_1$ to $C_{10}$ alkyl, $R^5$=$C_{10}$ to $C_{22}$ saturated or unsaturated hydrocarbon radical and X=halide (preferably chloride or bromide), carboxylate (acetate, glycolate), sulfonate, hydroxide, sulfate, or phosphate.

The organosilane quat is contained in an amount of up to about 5%, normally about 1 to 5%, and the hydrogen peroxide is in an amount up to about 20%, preferably about 3 to 10%, in a deionized aqueous media. The pH of the aqueous media is about 2 to about 9, preferably acidic about 3 to 5. The composition may further contain a solvent selected from the group of an alcohol, polyol, glycolether and mixtures thereof, as mentioned above, more preferably, methanol, ethanol or isopropanol.

The cationic monomeric organosilane quaternary ammonium compound is selected from the group consisting of 3-(trimethoxysilyl)propyldimethyloctadecyl ammonium chloride ("C-18 quat"), 3-(trimethoxysilyl)propyldimethyldodecyl ammonium chloride ("C-12 quat"), 3-(trimethoxysilyl)propyldidecylmethyl ammonium chloride, 3-(trimethoxysilyl)propyltetradecyldimethyl ammonium chloride, 3-(trimethoxysilyl)propyldimethylsoya ammonium chloride, 3-(trimethoxysilyl)propyldimethyloleyl ammonium chloride, 3-(trimethoxysilyl)propyloctadecyl ammonium chloride, 3-(trimethoxysilyl)propyloleyl ammonium chloride, and 3-(trimethoxysilyl)propyldocosane ammonium chloride. Other suitable organosilane quats may be used, providing they function to therapeutically treat skin in accordance with the principles of this invention.

In the preferred compositions of this invention the organosilane quaternary ammonium compounds facilitate the cleaning of the skin and also provide reactive groups for bonding with the skin to obtain the desired therapeutic effects. Accordingly, it is preferred for the organosilane to have a hydrocarbon group such as a $C_{10}$-$C_{22}$ saturated or unsaturated hydrocarbon group which facilitates healing, cleansing, surfactant, water repellent, and/or antimicrobial activities.

Suitable quaternary organosilanes are described in further detail with reference to the following Examples. As stated above, in general, the compositions contain the organosilane quat in an amount up to about 5% by weight, preferably up to 1% by weight. When skin compositions are formulated for cleaning dirt, grease or grime, etc., various types of abrasive particles in an amount up to 35% by weight may be used, preferably about 5 to about 25% by weight. When hydrogen peroxide or a complex thereof is employed, in general, the hydrogen peroxide content thereof is in an amount of up to about 20% by weight, preferably about 3 to about 10% by weight of the composition. More specific amounts for the most preferred organosilane quats, like 3(trimethoxysilyl)propyldimethyloctadecyl ammonium chloride, are about 0.4 to about 0.7% by weight and up to about 5% by weight with about 3% to 10% by weight of hydrogen peroxide.

Abrasive Solid Particles

As stated above, when therapeutic and/or prophylactic compositions are formulated to rid the skin of dirt, grime, grease, etc., or other soil, abrasive solid particles can be used.

Non-limiting examples of abrasive solid particles (grits) are shown on the following Table 1.

TABLE 1

| Abrasive Solid Particles |
| --- |
| Talc |
| Diatomaceous Earth |
| Vermiculite |
| Hydrated Alumina |

TABLE 1-continued

| Abrasive Solid Particles |
| --- |
| Mica |
| Calcite |
| Barium Sulfate |
| Fluorite |
| Wollastonite |
| Zeolite Spheres (Glass) |
| Barite |
| Pumice |
| Titanium Dioxide |
| Quartz (Silica) |
| Ceramic Microspheres |
| Zircon |
| Silicone Carbide |
| Aluminum Oxide |
| Plastics (polyethylene, polyester, polypropylene, etc.) |

Most grits are available in many different particle sizes, and generally have an average particle size of about 5 to about 300 microns, with their abrasive quality generally varying inversely with their particle size, i.e., the smaller their size, the less abrasive their action on the soil and the underlying skin surface. Moreover, due to the varying structure of grits (i.e., spherical, plate like, hollow, sharp, etc.), it is often desirable to employ a combination of grits of varying size and hardness to achieve the desired ability to remove both organic and inorganic soil from skin surfaces.

The grits must be nonreactive with the organosilane quat and the hydrogen peroxide or, if normally reactive, must be used in a form which has been rendered nonreactive with various available coatings; whereby the organosilane quat remains storage stable and available for bonding to the cleansed skin surface. Generally, the abrasive particles in the compositions are in an amount up to about 35% by weight where the organosilane quaternary compound is in an amount up to about 5% by weight. More preferably the abrasive particles are usually in an amount from about 5 to about 25% by weight where the quaternary compound is in an amount up to about 5% by weight.

Hydrogen Peroxide and Synergistic Activities

Hydrogen peroxide is a heavy liquid, and is available in aqueous solutions of various strengths. The anhydrous form is soluble in water and alcohol. It is unstable, but is commonly inhibited in solution by acetophenetidin, acetanilide or tin compounds, and is suitable for use in this invention in effective amounts as set forth above.

In our '313 application, we previously reported synergistic activities for the combination of the organosilane quat and hydrogen peroxide on various solid and porous surfaces. It is believed that the mechanism for these active ingredients applies to the treatment of skin according to the principles of this invention.

While not desiring to be bound by theory, it is believed helpful for a further understanding of the invention to postulate a mechanism by which the cationic organosilane quaternary compound is bonded to the skin surface in the presence of hydrogen peroxide. Hydrogen peroxide is well known for its antimicrobial activity and its oxidizing power which has been used to destroy a variety of toxic pollutants. In aqueous solution it is a stronger acid than water with reference to the following equation:

$$HOOH \rightarrow H^+ + HOO^-$$

Quaternary ammonium compounds are known to bond to anionic surfaces by interaction with absorbed water on the surface. This can be described by the following equation.
Surface-$H_2O$+$M^+$(aq)+$X^-$(aq)→Surface-$OH^-M^+$+$X^-$(aq)+

H+(aq) wherein M+ is an organic cation other than hydrogen ion and a hydrogen ion is displaced from the adsorbed surface water to become hydrated and to enter the aqueous phase as H+(aq). Thus the organic cation (M+) is "hydrogen bonded" to the anionic surface.

However, it has not been known before this invention to combine hydrogen peroxide with an organosilane quat to obtain the skin therapeutic effects of this invention as demonstrated in the Examples which follow.

The treatment and prevention of the skin disorders and conditions in the Examples is very remarkable and advantageous. The results achieved are considered to be unexpected and are believed to be synergistic, similar to synergism previously reported in our earlier '313 application.

In order to understand the remarkable and advantageous activities that have been demonstrated in the following Examples of this invention, it is believed that hydrogen peroxide, which is very similar to water, will be adsorbed onto the skin surface in a similar manner as demonstrated by the following equation:

Surface-HOOH+M+(aq)+X−(aq)→Surface-OOH−M+ + X−+H+(aq) wherein M+ is an organic cation other than H+, and H+ is displaced from adsorbed surface hydrogen peroxide to become hydrated and to enter the aqueous phase as H+(aq). It is believed that the organic cation (M+) is thus hydrogen bonded to the anionic skin surface associated with the hydroperoxide ion (—OOH−) even stronger than when associated with the hydroxide ion (—OH−) when water is on the anionic skin surface.

The organic cation also contains a silane function (—Si—OR) which can hydrolyze to a silanol (—Si—O—H), additional bonding of a chemical nature can occur with the substrate silanols, or reactive moieties on the skin surface, or to another organic cation silanol which would lead to polymerization and crosslinking of the organo quaternary compounds on the skin surface. This chemical bonding and crosslinking lead to a more durable coating which is not easily removed from the skin by ordinary contact (by clothing or use) or rinsing.

Non-limiting forms of hydrogen peroxide include urea peroxide, sodium percarbonate, calcium peroxide, magnesium peroxide and ammonium fluoride peroxohydrate, which solubilize or decompose in aqueous solution to form hydrogen peroxide.

With the additional cleaning, antimicrobial, and surface-activating capability of hydrogen peroxide on skin and its ability to strengthen the hydrogen bonding of the silane quaternary cation (M+) to the skin surface, thus facilitating the enhanced chemical bonding of the silane to the skin through condensation and subsequent crosslinking, an improved surface bonding or durability of the coating results from application of the compositions of this invention. Based upon our earlier findings in the '313 application, as stated above, it is believed that the combination of the cationic organosilane quaternary compound with hydrogen peroxide provides synergistic therapeutic and/or prophylactic effects on the skin. In other words, the resultant bonding and durability of this combination of components unexpectedly exceeds the summation of the individual components' activities.

Liquid Diluent

In a preferred form, the therapeutic compositions of this invention are liquids and require a liquid diluent. The preferred liquid diluent is water, most preferably deionized water, and/or an alcohol, which forms a medium for a slurry, cream or a gel with the organosilane quat and hydrogen peroxide. As developed above, nonreactive abrasive solid particles may be used to assist in cleansing the skin. Accordingly, the above stated relative amounts of the organosilane quat and abrasive solid particles, and hydrogen peroxide, are provided with a balance of deionized water to form the slurry, cream or gel with other potential additives such as thickeners, gelling agents, abrasive solids, lubricants and solvents. When the composition contains a solvent, it is usually selected from the group of an alcohol, polyol, glycol ether and mixtures thereof, more preferably ethanol or isopropanol.

The invention may be more readily understood by the following detailed disclosure of preferred embodiments of the invention. It is to be understood that the terminology used herein is for the purpose of describing particular embodiments and is not intended to be limiting. For the purpose of a clear understanding, the following terms, as used herein, are defined:

"abrasive" or "abrasion" mean any material or substance used for massaging of the skin, or the spot or area on a skin surface that results from being rubbed, agitated or massaged with abrasive "particle(s)" or "grit(s)".

"antimicrobial" means the ability of a skin surface and its coating to resist the attachment and growth of microorganisms; particularly those that are disease-causing.

"application", "applying" or "applied" as used herein means the treatment of skin with the composition, usually a slurry, cream or gel as topically applied.

"bacteria" means ubiquitous one-celled organisms that appear singly or in chains and are comprised of various species involved in fermentation, putrefaction and infectious diseases.

"bond", "bonded" or "bondable" means the ability to strongly adhere the composition to the skin surface, as in the ability to bond a water and soil repellent coating or characteristic to an otherwise water and soil accepting skin surface. As used herein, the composition is deemed "bonded" or "bondable" when it demonstrates contact angles to plain (tap) water that are superior (greater than about 25°) to untreated skin surface, and is resistant to removal by repeated rinsing with such water.

"clean", "cleansed", "cleanser" and "cleansing" either refers to skin surfaces that are unsoiled, unstained and free from soil buildup or the compositions of this invention and the methods of using them.

"disinfect(ed)" or "disinfecting" means any chemical agent used on skin surfaces to destroy or inhibit the growth of harmful organisms (germs) and the effects thereof.

"durable" or "durability" means long-lasting and not easily removed by rinsing with plain (tap) water.

"everyday soil" or "soil" means the dirt, grime, grease, stains, spills, splatters and blemishes on skin that result from working, cooking, eating, drinking, washing, bathing and showering such as dirt, dust, beverages, milk, coffee, tea, juices, sauces, gravies, food boil over, soap scum, water spots, mineral deposits, etc.

"germ(s)" means disease-producing microorganisms.

"inorganic soil" means lime scale, hard water film, rust and mineral deposits composed of matter that is not animal or vegetable; derived from mineral sources.

"massaging" refers to wiping and/or scrubbing the composition on and into the buildup until the soil is no longer attached to the skin surface.

"microorganism(s)" means any organism too small to be viewed by the unaided eye, such as bacteria, protozoa, virus and some fungi and algae.

"mitigate(d)" means to lessen in force or intensity and make less severe; to mollify and control; particularly with respect to the attachment and growth of microorganisms.

"mold" and "mildew" mean the growth of minute fungi that forms on animate and inanimate surfaces and is generally associated with dampness and/or decay.

"monomer" or "monomeric" means a molecule capable of reacting with identical or different molecules or to form a protective coating on skin.

"multifunctional" means the process of achieving two or more discernable results from a single application, as in simultaneously or sequentially cleaning and coating the skin whereby the coating also performs the function(s) of rendering the skin water repellent, soil repellent, moisture transmissive and/or antimicrobial, all to promote healing.

"nonreactive" refers to abrasive solid particles that do not react with the organosilane quaternary or hydrogen peroxide so as to diminish their therapeutic cleansing and coating proportions in accordance with this invention; or, if reactive in their normal state, are coated with a variety of substances that form a barrier to make them nonreactive and storage stable to provide the desired skin surface therapeutic cleansing and bonding functions.

"organic soil" means foodstuff, soap scum, grease, oil and any chemical compound containing carbon; having the characteristics of or derived from living organisms.

"particle(s)" and "grit(s)" means minute pieces or fragments of solids with varying hardness, structure, texture and size used for the removal of insoluble soil.

"prophylactic(ally)" refers to a protective effect, process and/or quality achieved by the therapeutic compositions of this invention.

"polymer" or "polymeric" means a compound of high molecular weight usually derived by the reaction/condensation of many smaller molecules.

"repel" or "repellent" means to resist effectively, to keep off or out, to fail to mix with and to resist the absorption, attachment or passage of water, soil and germs.

"resistant to removal" means a coating or skin surface finish that is not easily removed by everyday use of the treated skin on body surfaces, ordinary contact with clothing or by rinsing, washing or cleaning with plain (tap) water.

"sanitizer" or "sanitizing" means a substance, preparation or process for cleaning a skin surface to render it free of from dirt, soil, germs, etc.

"soil repellent" means a skin surface that exhibits reduced adhesion to, and buildup of, for example, everyday soil both before and after evaporation of the water component.

"sterilant" or "sterilization" means any chemical agent, substance or process that causes the destruction of living microorganisms.

"storage stable" refers to a useful shelf life of the liquid compositions of this invention when stored in containers under ambient environmental conditions of temperature as found in warehouses, shipping containers, packages, etc., up to 120° F. for months, typically desired for more than six months or at least one year.

"skin" or "skin surface" refers to the organ of an animal or human body that covers part of, or the entire, body surface and is composed of two main layers: the surface epithelium or epidermis which includes the uppermost stratum corneum and the subadjacent connective tissue layer or dermis. These terms are also meant herein to refer to nails and hair.

"skin disorder(s)" or "disorder(s)" refers to skin whose health and/or integrity is compromised by wounds, abrasions, ulcers, burns, infections, irritations, microbes, soil, water, psoriasis, acne vulgaris, blemishes, age spots, sclerosis, other physical or chemical injuries, and other skin deficiencies including eruptions.

"surfactant" refers to a substance that reduces surface tension or interfacial tension between two liquids or a liquid and solid. It includes detergents, wetting agents and emulsifiers.

"therapeutic(ally)" refers to a remedial, prophylactic, or curative effect, process and/or quality achieved by the inventive composition(s) and method(s) on skin disorder(s).

"virus" means an ultramicroscopic, metabolically inert infectious agent that replicates only within the cells of living hosts, mainly bacteria, plants and animals, but which are transferred by hand & body contact directly or indirectly through hand & body contact surfaces.

"water repellent", "water repellency" and "hydrophobic (ity)" as used herein describe the hydrophobic nature or characteristic of skin and its ability to repel water as measured by the contact angle of a drop or droplet of plain (tap) water on the surface. Generally, the hydrophobicity of a discrete skin surface is rated in terms of its contact angle to plain (tap) water drops that are greater than about 25°, and its resistance to removal by repeated rinsing with such water.

EXAMPLES

Skin Care Tests on Hands, Face, Feet, and Other Body Parts

Many skin disorders are caused by both transient and resident eruptions and blemishes on the outer skin layer or in hair follicles, nails and gland openings. Whether the source is internal or external resulting from cuts, bruises and abrasions, healing is frequently delayed by the attachment and growth of bacteria, virus and fungi that find normal body excreta, warm body temperatures, moisture and living tissue to be an ideal, nutritious environment.

The therapeutic compositions of this invention were successfully employed to treat the following skin disorders and conditions as reported on Tables 2 and 3.

TABLE 2

| | Composition |
|---|---|
| #1 | .4% C-12 quat, 3% hydrogen peroxide, 4% denatured ethanol, deionized water |
| #2 | 1% C-18 quat, 3% hydrogen peroxide, 6% isopropyl alcohol, deionized water |
| #3 | 2% C-18 quat, 4% hydrogen peroxide, deionized water |
| #4 | 3% C-18 quat, 6% hydrogen peroxide, deionized water |
| #5 | 4% C-18 quat, 8% hydrogen peroxide, deionized water |
| #6 | 5% C-18 quat, 10% hydrogen peroxide, deionized water |
| #7 | 5% C-18 quat, 20% hydrogen peroxide, deionized water |
| #8 | 2% C-18 quat, 20% hydrogen peroxide, deionized water |

TABLE 3

| Composition | Disorder | Treatment/Duration | Result |
|---|---|---|---|
| #2 | Toe nail fungus | 3 drops* 2x day/1 week followed by composition #1 on a daily basis | Fungus softened - 90% reduced, nail growing normally |
| #1 | Foot odor | Spray** & wipe to spread Daily | Foot odor virtually eliminated |
| #1 | Hand & foot calluses | Spray** & wipe to spread Daily | Calluses gradually softened and eliminated |
| #6 | Elbow & Cradle Cap Psoriasis | 3 drops* 2x day/2 weeks | Psoriasis gradually eliminated (hair lightened |

TABLE 3-continued

| Composition | Disorder | Treatment/Duration | Result |
|---|---|---|---|
| | | | to blond, but returned to normal color in two/three weeks - psoriasis has not returned) |
| #7 | Skin tag (eye lid, nose) | 2 drops* Nightly/2 weeks | Skin tag fell off |
| #4 | "Age spots" (hands, face) | 2 drops* Nightly/10 days | Spots lightened to skin color |
| #5 | Pimples/zits/blackheads | 2/3 drop* 2x day/3 days | Pimples/zits dried, blackheads expelled |
| #6 | Suspected basal cell carcinoma | 2 drops* 2x day/7 days | Growth stopped or apparently stopped |
| #3 | Paper cuts on hands | 3 drops* 2x day/5 days | Cuts healed without infection |
| #2 | Knee abrasion | 3 drops* 2x day/5 days | Abrasion healed without pain/infection |
| #1 | "Jock itch" | Spray** & wipe to spread 5 days | Itching eliminated/rash gradually reduced |
| #1 | Puncture wound/Infection | Spray** & wipe to spread 7 days | Wound healed, infection eliminated |
| #8 | Subcutaneous eruption | 2 drops* 2x day/10 days | Eruption subsiding |

*"drops" means a saturated q-tip sufficient to wet area being treated, which normally approximates an application of about 0.15 to 0.2 ml.
**"spray" means an atomized application sufficient to wet area being treated, which normally approximates an application of about 0.5 ml. to about 4 ml depending upon area treated.

Tables 2 and 3 demonstrate the remarkable and advantageous therapeutic effects of the storage stable compositions of this invention. In addition to the results recorded in Table 3, skin of the hands, feet, knees, etc., that was treated with the compositions was cleansed and rendered hydrophobic. The skin surfaces were disinfected of germs, mold, virus or microorganisms, or their activities were mitigated. Cleansing of organic/inorganic soil and sanitizing the skin was improved by massaging the skin with the addition of non-reactive abrasive particles in an amount of from about 5% to 25% by weight of the compositions. It was also found upon treating the skin in accordance with the above Examples, that skin hydration was regulated by providing a moisture transmissive coating on the skin as a result of the therapeutic treatment. Thus, the inventive compositions provided a durable therapeutic multifunctional coating that rendered the skin water and soil repellent, and antimicrobial. As further evidence of the antimicrobial therapeutic effects of the compositions, provided hereinafter are examples of antimicrobial efficacy of the organosilane quats and hydrogen peroxide.

Examples—Antimicrobial Efficacy of Cationic Organosilane Quaternary Ammonium Compound/Hydrogen Peroxide Composition of Tile Surfaces These tests determine the antimicrobial efficacy of the compositions of this invention on tile surfaces contaminated with a mixture of microbiological organisms consisting of *Escherichia coli*, *Staphylococcus aureus* and *Bacillus subtilis*. The composition tested was similar to composition #2 (Table 2) consisting of 0.4% 3-(trimethoxysilyl)propyldi-methyloctadecyl ammonium chloride with 3% hydrogen peroxide. The following Materials and Methods were employed to conduct the tests.

Materials
 i. Microorganisms:
  a. *Escherichia coli* (ATCC 11229)
  b. *Staphylococcus aureus* (ATCC 25923)
  c. *Bacillus subtilis* (ATCC 6363)
 2. Media:
  a. Blood agar plate (BAP); Tryptic Soy Agar amended with 5% defibrinated sheep blood
  b. Butterfield's Buffer (BFB)
 3. McFarland Turbidity Standard (VWR)
 4. Sterile Supplies:
  a. Sterile swabs
  b. Micropipette and sterile tips
 5. Equipment:
  a. Incubator
  b. Spiral Biotech Autoplate 4000
 6. Paper towels
 7. Tile surfaces
 8. Example 1 composition (cationic organosilane quaternary ammonium compound with hydrogen peroxide) for testing Methods
 1. The Blood Agar Plates (BAP) were inoculated with fresh cultures of the test organisms to obtain confluent growth and incubated at 35° C. for 24 hours. A suspension of each organism was prepared by transferring colonies of each organism into separate 10 ml tubes of Butterfield's buffer. The suspensions were adjusted to a turbidity of 0.5 McFarland units, corresponding to approximately $1\times10^6$ cells.
 2. A 1:100 dilution of each suspension was performed by aliquoting 0.1 ml of suspension into 10 ml BFB, creating organism suspensions.
 3. To ensure no background microbial contamination was present, all test surfaces were cleaned with isopropyl alcohol and allowed to air dry.
 4. Duplicate 100 cm² areas were measured and designated on the test surfaces for each organism and labeled using masking tape.
 5. Test areas were sampled with BFB pre-moistened sterile swabs to confirm test areas were negative for bacterial growth.
 6. Using a micropipette and sterile tips, 0.1 ml of the organism suspensions were applied independently to the corresponding sections of the test surfaces and evenly distributed using a flame sterilized glass rod to cover the entire 100 cm².
 7. Each surface was then treated with the composition of Example 1 by spraying it onto the surface to be cleaned and wiping with paper towel or soft cloth until crystal clear and sparkling."
 8. Test areas were sampled with BFB pre-moistened sterile swabs.
 9. The organism suspensions and test sample swabs were vortexed to ensure homogeneity and cultured onto BAP via the Spiral Biotech Autoplate 4000.
 10. The cultured samples were incubated at 35° C. for 48 hours. Plates were examined and organisms enumerated.

Results
The analytical data for the tile surface are shown below in Table 7.

TABLE 4

| Organism | Negative Surface Control CFU/100 cm² | Organism Inoculum (0.1 ml of Organism Suspension) CFU/ml | Treated Surfaces CFU/100 cm² |
|---|---|---|---|
| E. coli | <10 | $2.88 \times 10^2$ | <10 |
| E. coli | <10 | $2.88 \times 10^2$ | <10 |
| S. aureus | <10 | $3.44 \times 10^2$ | <10 |
| S. aureus | <10 | $3.44 \times 10^2$ | <10 |

TABLE 4-continued

| Organism | Negative Surface Control CFU/100 cm$^2$ | Organism Inoculum (0.1 ml of Organism Suspension) CFU/ml | Treated Surfaces CFU/100 cm$^2$ |
|---|---|---|---|
| B. subtilis | <10 | 7.27 × 10$^2$ | <10 |
| B. subtilis | <10 | 7.27 × 10$^2$ | <10 |

The negative control data demonstrates that all surfaces were free of bacteria prior to the experiment. The results indicate that the composition is an effective bactericide against *Bacillus subtilis, Staphylococcus aureus*, and *Escherichia Coli*.

Example—Durability of the Therapeutic Coating on Skin

The therapeutic coating on the skin was tested for durability on hands in the following manner.

1. Hands were washed with "Ivory" soap, rinsed with tap water and dried with a paper towel.
2. The back of one hand was then sprayed with the following composition:
   0.4% C-18 quat
   3.0% hydrogen peroxide
   4.0% denatured ethanol
   in deionized water The excess was shaken off and the hand was allowed to air dry.

3. The dried back of the hand was then rinsed with 23 degree centigrade tap water followed by shaking to remove excess water. A repellent skin surface was noted in view of the 80 to 90 degree contact angle of the remaining droplets of water.
4. The treated hand was re-rinsed 20 times without apparent change in the contact angle of the residual water drops.

The results demonstrate the excellent durability of the therapeutic coating of this invention on the surface of the skin.

Example—Moisture Transmissive Test

The following test was employed to demonstrate the moisture transmission of skin treated with the compositions of this invention compared to untreated skin:

Collagen film (0.15 mm thick) was employed as a substitute for skin (Ref.: U.S. Pat. No. 5,300,286 to Dow Corning, Col. 6, Example 1). Collagen film sheet was rinsed on both sides with isopropanol and allowed to air dry. The compositions employed in the teat were then sprayed on one side of the film and completely wetted the surface of the film. The excess of the composition was removed with a paper towel and the treated film surface allowed to air dry. Samples of the film were cut into 2½-inch diameter test samples.

The test equipment employed in the Moisture Transmissive Test was a "Mason" Jar with a 2½-inch diameter opening and a capacity of about 8 oz. The film samples were placed on the top of the opening of the jar followed by a rubber gasket in place of the "Mason" jar seal. The lid was then attached to seal the collagen film in place. 10 ml of tap water were added to the surface of the film and the film was maintained with a water coating on the surface throughout the test period. 50 ml of concentrated sulfuric acid had been added to each test jar as a desiccant to absorb the water moisture that would pass through the film. The weight gain of the sulfuric acid would be equal to the amount of water passing through the collagen film in a given amount of time. The weight gain was determined by the difference between the weight of the jar and acid the jar before and after the test period.

Treated films were tested with the treated surface on top and in contact with the water (95-hour test) and also with the treated surface on the bottom with the untreated surface in contact with the water (7-hour test). A control with no treatment of the surface was also run.

The following compositions of this invention were tested and the results are presented in Table 5 as follows:

Composition No. 1: 0.4% C-12 quat, 3.0% hydrogen peroxide, 4.05 denatured ethanol in deionized water.

Composition No. 2: 0.4% C-18 quat, 3.0% hydrogen peroxide, 4.0% denatured ethanol, in deionized water.

TABLE 5

| Composition | 1 | 2 | Control |
|---|---|---|---|
| 7-hour test period | 2.22 gms | 2.09 gms | 2.27 gms |
| 95-hour test period | 7.42 gms | 8.00 gms | 7.42 gms |

It may be concluded that the moisture transmissiveness of the treated collagen films (representative of human skin) is maintained at essentially the same level when treated with the compositions of this invention as the untreated film.

Those of ordinary skill in the art realize that the descriptions, procedures, methods and compositions presented above can be revised or modified without deviating from the scope of the described embodiments, and such do not depart from the scope of the invention.

What is claimed is:

1. A storage stable and skin bondable therapeutic composition for treating a skin disorder comprising
   a cationic organosilane quaternary ammonium compound having a $C_{10}$-$C_{22}$ saturated or unsaturated hydrocarbon group, and
   hydrogen peroxide in aqueous media, said components in synergistically effective amounts for binding with the skin, said storage stable composition providing a bondable and durable moisture transmissive coating on the skin.

2. The composition of claim 1 wherein said quaternary compound is present in an amount of about 1 to about 5% by weight and said hydrogen peroxide is present in an amount of about 3 to about 10% by weight.

3. The composition of claim 1 which further contains a solvent selected from the group of an alcohol, polyol, glycolether, and mixtures thereof.

4. The composition of claim 3 wherein the polyol or alcohol is a glycol, ethylene glycol monobutyl ether, methanol, ethanol or isopropanol.

5. The composition of claim 1 where the aqueous media is acidic.

6. The composition of claim 5 where the pH is on the order of about 2 to about 5.

7. The composition of claim 1 wherein the aqueous media is deionized water.

8. The composition of claim 1 wherein said quaternary compound is defined by the formula

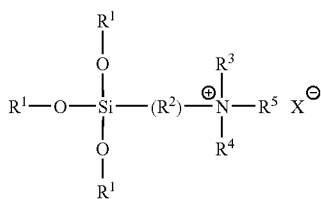

wherein $R^1$=hydrogen and/or $C_1$ to $C_4$ alkyl; $R^2$=divalent hydrocarbon radical with $C_1$ to $C_8$ carbon atoms, $R^3$=hydrogen or $C_1$ to $C_4$ alkyl, $R^4$=hydrogen or $C_1$ to $C_{10}$ alkyl, $R^5$=$C_{10}$ to $C_{22}$ saturated or unsaturated hydrocarbon radical and X=halide, carboxylate, sulfonate, hydroxide, sulfate, or phosphate.

9. A storage stable and skin bondable therapeutic composition for treating a skin disorder comprising a cationic organosilane quaternary ammonium compound in an amount of about 0.4% to about 5% by weight defined by the formula:

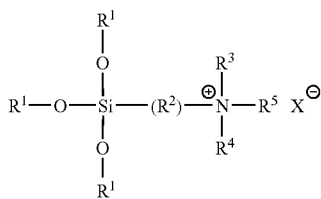

wherein $R^1$=hydrogen and/or $C_1$ to $C_4$ alkyl; $R^2$=divalent hydrocarbon radical with $C_1$ to $C_8$ carbon atoms, $R^3$=hydrogen or $C_1$ to $C_4$ alkyl, $R^4$=hydrogen or $C_1$ to $C_{10}$ alkyl, $R^5$=$C_{10}$ to $C_{22}$ saturated or unsaturated hydrocarbon radical and X=halide, carboxylate, sulfonate, hydroxide, sulfate, or phosphate, and hydrogen peroxide in an amount of about 3% to about 20% by weight in acidic deionized aqueous media, said components in synergistically effective amounts for binding with the skin, said storage stable composition providing a bondable and durable moisture transmissive coating on the skin.

10. The composition of claim 9 wherein the pH of the acidic media is about 2 to about 5.

11. The composition of claim 9 which further contains a solvent selected from the group of an alcohol, polyol, glycolether and mixtures thereof.

12. The composition of claim 9 which further contains an alcohol selected from the group consisting of methanol, ethanol, and isopropanol.

13. The composition of claim 9 wherein said organosilane quaternary ammonium compound is selected from the group consisting of 3-(trimethoxysilyl)propyldimethyloctadecyl ammonium chloride,
3-(trimethoxysilyl)propyldidecylmethyl ammonium chloride,
3-(trimethoxysilyl)propyltetradecyldimethyl ammonium chloride,
3-(trimethoxysilyl)propyldimethylsoya ammonium chloride,
3-(trimethoxysilyl)propyldimethyloleyl ammonium chloride,
3-(trimethoxysilyl)propyloctadecyl ammonium chloride,
3-(trimethoxysilyl)propyloleyl ammonium chloride, and
3-(trihydroxysilyl)propyldimethyloctadecyl ammonium chloride.

14. The composition of claim 9 wherein the organosilane quaternary ammonium compound is selected from the group consisting of 3(trimethyoxysilyl)dimethyloctadecyl ammonium chloride and 3(trimethoxysilyl) propyldimethyldodecyl ammonium chloride in an amount of from about 1 to about 5° A) by weight and the hydrogen peroxide is in an amount of about 3 to about 10% by weight.

15. A composition of claim 9 wherein the skin disorder is selected from the group consisting of wounds, abrasions, ulcers, burns, infections, irritations, psoriasis, acne vulgaris, blemishes, age spots, sclerosis, and skin disorders caused by water, soil, and/or microbes.

16. The composition of claim 9 wherein said skin disorder is caused by water, soil and/or microbes, and said binding to the skin results in a multifunctional coating onto said skin thereby rendering the skin water repellent, soil repellent and/or antimicrobial.

17. The composition of claim 9 wherein the skin disorder is microbial contaminated skin and said binding to the skin is effective to render the skin antimicrobial.

18. The composition of claim 9 which additionally contains abrasive particles in an amount up to 35% by weight.

19. The composition of claim 18 which additionally contains abrasive particles in an amount from about 5% to about 25% by weight.

20. The composition of claim 19 wherein said abrasive particles are nonreactive coated or uncoated particles from the group consisting of silicas ($SiO_2$), silicates, metal oxides, metal carbonates, clays, carbides, and plastics, having an average size on the order of about 5 to about 300 microns.

21. The composition of claim 9 formulated as a cream, lotion, gel, ointment, or spray.

22. The composition of claim 1 wherein said quaternary compound is present in an amount up to 5% by weight and said hydrogen peroxide is present in an amount up to about 20% by weight.

* * * * *